United States Patent [19]

Imai

[11] Patent Number: 4,769,467

[45] Date of Patent: Sep. 6, 1988

[54] FLUOROGENIC 2,1,3-BENZOXADIAZOLES AND FLUOROMETRIC AMINE/THIOL ASSAYS THEREWITH

[75] Inventor: Kazuhiro Imai, Tokyo, Japan

[73] Assignee: Oread Laboratories, Inc., Lawrence, Kans.

[21] Appl. No.: 729,203

[22] Filed: May 1, 1985

[30] Foreign Application Priority Data

Sep. 28, 1983 [JP] Japan .................. 58-178313

[51] Int. Cl.⁴ .................. C07D 271/12; G01N 33/00
[52] U.S. Cl. ........................ 548/126; 436/63
[58] Field of Search ............ 548/126; 436/63

[56] References Cited

FOREIGN PATENT DOCUMENTS

| 59-51270 | 3/1984 | Japan | 424/7.1 |
| 60-72874 | 4/1985 | Japan | 424/7.1 |
| 431166 | 1/1975 | U.S.S.R. | 548/126 |

OTHER PUBLICATIONS

Toyo'oka, Ann. Chem. 56, 2461 (1984).

*Primary Examiner*—Robert Gerstl
*Attorney, Agent, or Firm*—Burns, Doane, Swecker & Mathis

[57] ABSTRACT

Fluorogenic compounds are disclosed which are reactive with biologically important analytes including primary amines, secondary amines, and/or thiols and are of the general formula:

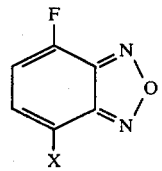

wherein X is a group such as $-\overset{\|}{C}-CH_3$, $-CN$, $-CO_2CH_3$, or $SO_2R$, and wherein R is

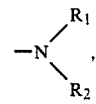

$OR_3$, or Cl; $R_1$ and $R_2$ are hydrogen atoms or alkyl groups having 1 to 3 carbon atoms and $R_3$ is a phenyl or benzyl group. The inventive compounds form a fluorescent adduct with the above analytes at the number 7 position of the benzoxadiazole ring. The fluorescent adduct thereby formed enables detection of very minute amounts of analyte (picomoles) using conventional fluorescent analytical methods.

9 Claims, 3 Drawing Sheets

Effect of pH on the fluorescence intensities of 2.3μ M ABD-homocysteine. Excitation wavelength 390 nm; Emission wavelength, 515 nm; buffers, 0.05 M Britton-Robinson (pH 2-10), 0.1 M HCl (pH 1)

ABD-F Adducts a   cysteine
b   glutathione
c   N-acetylcysteine
d   homocysteine
e   cysteamine

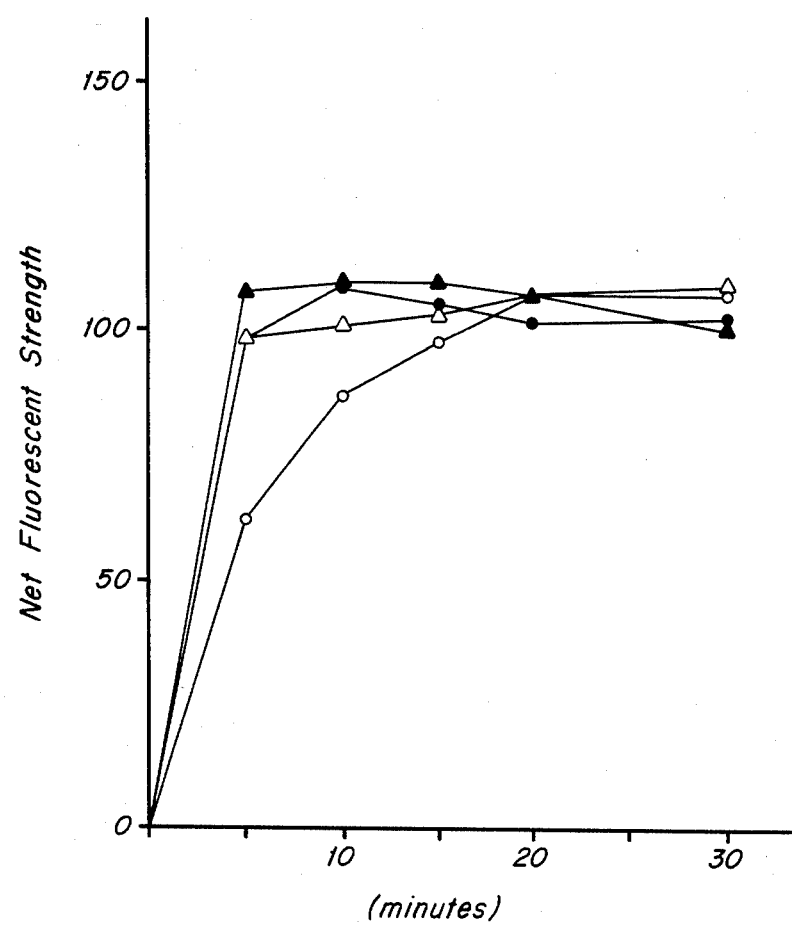

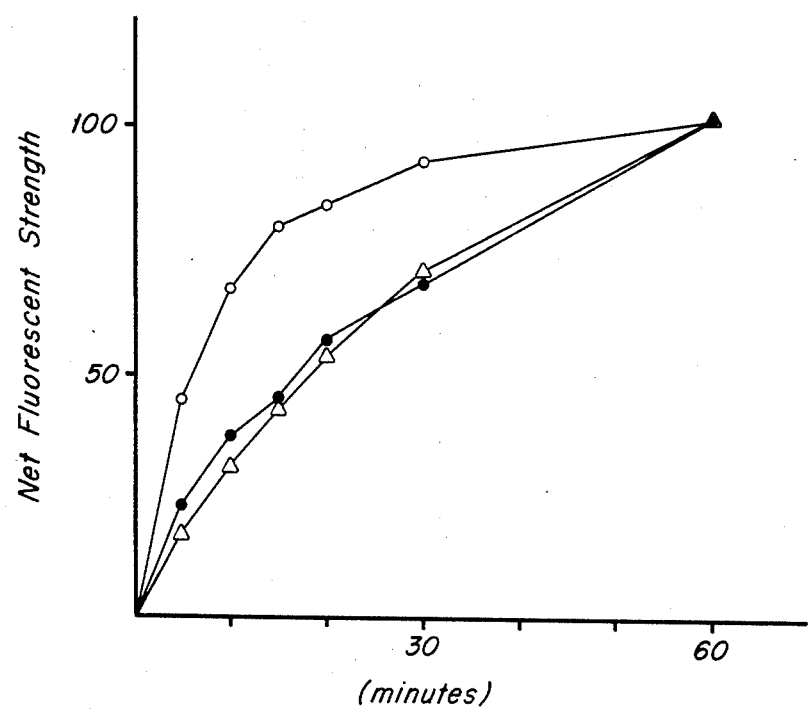

FLUOROGENIC 2,1,3-BENZOXADIAZOLES AND FLUOROMETRIC AMINE/THIOL ASSAYS THEREWITH

BACKGROUND OF THE INVENTION

1. Field of the Invention

The present invention relates to fluorogenic derivatives of 2,1,3-benzoxadiazoles and more specifically to compounds of the general formula:

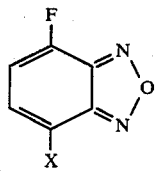

wherein X is

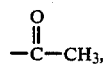

—CN,—CO$_2$CH$_3$ or SO$_2$R, and wherein R is

OR$_3$, or —Cl; R$_1$ and R$_2$ are hydrogen atoms or alkyl groups 1 to 3 carbon atoms, and R$_3$ is a phenyl or benzyl group. The invention also relates to a method of detecting and quantifying thiols as well as primary and secondary amines by reacting them with the above 2,1,3-benzoxadiazole derivatives to form a novel fluorescent product.

2. Description of the Prior Art

Assaying techniques wherein a fluorogenic reagent is reacted with a substrate to form a fluorescing adduct have been known for some time. Such techniques have been found to be particularly well-suited to biological assaying. Thus, in U.S. Pat. No. 4,045,487, a furanone compound is disclosed which, although non-fluorescent by itself, forms a fluorescent product when reacted with a primary amine. Although the fluorescent furanone complexes are readily detectable and quantifiable by conventional techniques, their practical application to biological media to be analyzed is limited due to the non-reactivity of the furanones with secondary amines and thiols. Thus, unless there is interest only in the detection and measurement of particular primary amines, other time consuming and potentially expensive techniques will be required in order to assay secondary amines as well as thiols.

The use of fluorogenic reagents has been found to increase the sensitivity of recently developed techniques in high performance liquid chromatography (HPLC), which enables more efficient separation of amino acids and thiols from biological fluids. While fluorogenic reagents such as fluorescamine and o-phthalaldehyde are well suited for the sensitive detection of amino acids having primary amino groups, they, like the furanone compounds described above, are not reactive with the imino acids (secondary amines) such as proline and hydroxyproline, and therefore do not form fluorescent complexes therewith. Thus, in order to assay imino acids with the above fluorogenic reagents, it is required that oxidizing reagents such as N-chlorosuccinimide or sodium hypochlorite be added first so as to convert the imino acids to primary amines. Such is not desirable in practice however since the presence of excess oxidizing reagents obstructs the fluorescence yield of the generated fluorophores.

The deleterious side reactions of the oxidizing agents as well as the undesirability of having to carry out the additional oxidation step led to the pursuit of compounds which would be capable of reacting directly with both primary and secondary amines and, optimally, thiols since such represent a significant portion of the compounds found in many biological solutions. To that end, derivatives of 2,1,3-benzoxadiazoles and more specifically, 7-fluoro-4-nitrobenzo-2,1,3-oxadiazoles (NBD-F) of the formula:

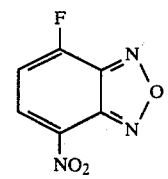

were developed. These compounds were observed to react with both primary and secondary amines as well as thiols. The reaction with secondary amines can be represented by the following:

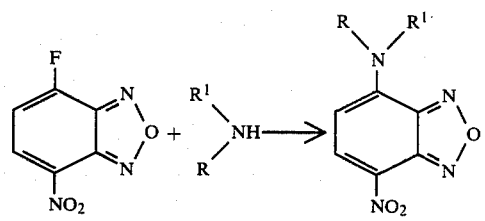

Thus, NBD-F reacts with primary amino acids such as asparagine, glutamic acid, serine, glycine, threonine and alanine as well as the secondary amino acids proline and hydroxyproline at a pH of 8. However, tryptophan, which is also a secondary amino acid cannot be assayed with NBD-F. NBD-F can also be used to selectively assay certain thiol compounds by modifying the reaction conditions used for amino and imino acid analysis. However, the degree of fluorescence of the products formed with the —SH bond is lower than that obtained with the —NH bond of primary and secondary amino compounds.

Although, as indicated, NBD-F is reactive with primary amines, certain secondary amines and certain thiols, it has not proven completely satisfactory for use as a fluorogenic reagent. More specifically, the fluorescent adduct formed from NBD-F and thiols is very unstable due to the S→N migration which occurs. Additionally, the sulfur adduct has a much lower fluorescent quantum yield making the detection thereof more difficult. Finally, NBD-F itself undergoes rapid hydrolysis thereby resulting in the formation of an additional peak in the chromatogram in addition to the plurality of peaks already present for the amino acid and thiol adducts. This additional peak is to be avoided since it potentially can interfere with the peaks of analytes thus making the analytical process that much more difficult.

Ammonium 7-fluoro-2,1,3-benzoxadiazole-4-sulfonate (SBD-F) as well as ammonium 7-chloro-2,1,3-benzoxadiazole-4-sulfonate (SBD-Cl) have also been employed for pre-column labelling of thiols in HPLC. SBD-Cl is a desirable fluorogenic reagent from the standpoint of water solubility as well as the stability of the SBD-thiol complex formed. Nevertheless, SBD-Cl has not proven totally satisfactory in thiol assaying techniques due to its relatively low reactivity with respect to thiol. More specifically, when SBD-Cl and thiol were reacted in an alkaline solution (pH=10) at 40° C. for one hour, and then at room temperature for 24 hours, only a few percent of the SBD-Cl had reacted with thiol. It was therefore impossible to ascertain the quantity of thiol present when in low concentrations.

SBD-F, like SBD-Cl, is highly soluble in water and forms highly stable fluorophores with the thiols. It also has a greater degree of sensitivity than does SBD-Cl and excellent fluorescent characteristics. However, the conditions necessary for completion of the reaction between the thiols and SBD-F are rather drastic, with the thiols being reacted with 100 fold excess reagent in an alkaline medium (pH 9.5) at 60° C. for 1 hour. Such drastic conditions should, if possible, be avoided due to the possible degradation of the thiols being analyzed.

SUMMARY AND OBJECTS OF THE INVENTION

In view of the foregoing limitations and shortcomings of prior art compounds as well as other disadvantages not specifically mentioned above, it should be apparent that there still exists a need in the art for a fluorogenic reagent which has a high and selective reactivity to primary and secondary amines as well as thiols present in a sample. It is, therefore, a primary objeive to fulfill that need by providing a 7-fluoro-2,1,3-benzoxadiazole compound which is substituted at the number four postion by a sulfonyl, acetyl, cyano or carboxymethyl group.

More particularly, it is an object of this invention to provide a novel set of fluorogenic reagents which are highly reactive to both amines (primary and secondary) and thiols, thus allowing detection of both.

It is a further object of this invention to provide a novel set of fluorogenic reagents exhibiting selective reactivity to amines and thiols.

Yet another object of this invention is to provide a novel set of fluorogenic reagents which will react with amines and thiols under relatively mild conditions.

Still another object of this invention is to provide a novel set of fluorogenic reagents which enables accurate detection of very low concentrations ($10^{-12}$ moles) of amino acids and thiols.

Another object of this invention is to provide fluorescent reagents which exhibit low background fluorescent emission and therefore have good measurement sensitivity.

An additional object of this invention is to provide fluorescent adducts which are highly stable in solution form.

A further object of this invention is to provide fluorescent adducts which are highly fluorescent.

Another object of this invention is to provide a method of assaying primary and secondary amines as well as thiols using the 7-fluoro-2,1,3-benzoxadiazole derivatives herein described in conjunction with HPLC as well as other separation techniques.

Briefly described, those and other objects of the invention are accomplished by providing a fluorescent reagent of the formula:

wherein X is

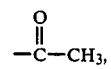

—CN,—CO$_2$CH$_3$ or SO$_2$R, and wherein R is

OR$_3$, or —Cl; R$_1$ and R$_2$ are hydrogen atoms or alkyl groups having 1 to 3 carbon atoms and R$_3$ is a phenyl or benzyl group. Preferably, X is —SO$_2$R. These reagents are themselves not fluorescent but react rapidly with primary and secondary amines as well as thiol compounds to yield a fluorescent adduct which may be readily detected and quantified and which is stable. In another aspect, the invention relates to a method of assaying amines and thiols using the reagents of the present invention as well as to the adducts themselves.

With the foregoing and other objects, advantages, and features of the invention that will become hereinafter apparent, the nature of the invention may be more clearly understood by reference to the following detailed description of the invention and the appended claims.

BRIEF DESCRIPTION OF THE DRAWINGS

FIG. 2 is a graph depicting the relationship between reaction time and fluorescent strength when ABD-F and SBD-SO$_3$ph are reacted with N-acetyl-L-cysteine at pH 8.0 and pH 9.5;

FIG. 3 is a graph depicting the effect of time on the net fluorescent strength when L-proline is reacted with SBD-SO$_3$ $_{1 ph}$, ABD-F and NBD-Cl.

DETAILED DESCRIPTION OF A PREFERRED EMBODIMENT

1. Preparation of the Fluorescent Reagents

Figure 1:
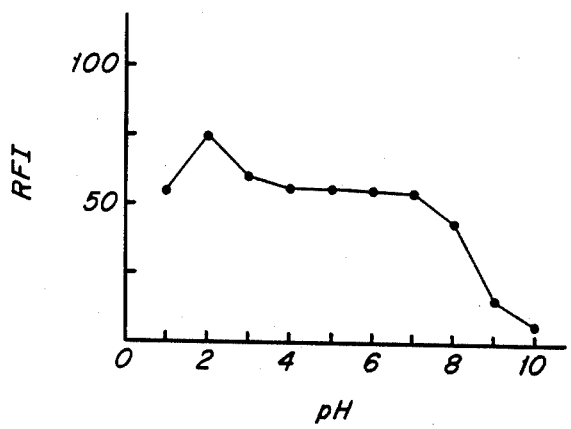
FIG. 1 is a graph depicting the effect of pH on the fluorescence intensities of ABD-homocysteine.

The functional groups substituted at the number 4 position of the 2,1,3-benzoxadiazole are electron withdrawing and make the fluorine at the number 7 position more reactive and capable of forming an adduct with primary amines, secondary amines and thiols. They are all derived from 7-fluoro-2,1,3benzoxadiazole of the formula:

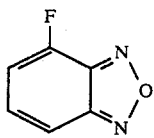

The above starting material is a known compound and may, for example, be prepared by the method of Nunno et al (J. Chem. Soc. (C)) 1433 (1970).

The sulfonyl substituted compounds of the formula:

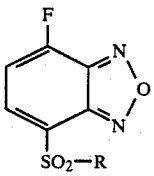

wherein R is

—OR$_3$ or —Cl and wherein R$_1$ and R$_2$ are hydrogen atoms or alkyl groups having 1 to 3 carbon atoms and R$_3$ is a phenyl or benzyl group, are prepared by the following reaction sequence.

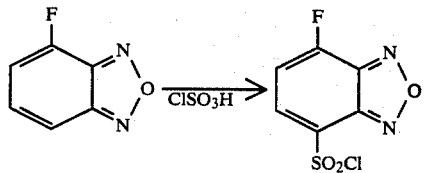  (I)

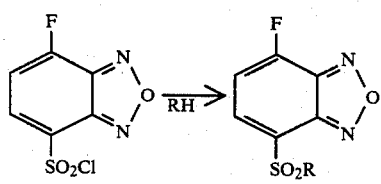  (II)

It will be appreciated that the "R" group of RH in Reaction (II) is as defined above with the exception of the chlorine atom.

In a preferred embodiment, R is NH$_2$ which corresponds to 4-Aminosulfonyl-7-fluoro-2,1,3-benzoxadiazole (ABD-F) which is described in the article "New Fluorogenic Reagent Having Halogenobenzofurazan Structure for Thiols: 4-(Aminosulfonyl)-7-fluoro-2,1,3-benzoxadiazole, *Analytical Chemistry*, 1984, 56, 2461 by Kazuhiro, Imai and Toshimasa Toyo'oka, the disclosure of which is hereby incorporated by reference. The sulfonyl substitute compounds are described in Japanese Patent Application 58-178313; Kazuhiro Imai, Applicant, the disclosure of which is also incorporated by reference.

Solvents which can be used in the above-described Reaction (I) include tetrahydrofuran, diethyl ether, acetonitrile, dioxane, chloroform, dichloromethane, dichloroethane, ethyl acetate and other inactive organic solvents. Solvents which can be used in Reaction (II) include such inert organic solvents as benzene, toluene, pyridine, ether, chloroform, and ethyl acetate. Both of the reactions may be carried out at a temperature range of 0°–110° C. although it is preferred to carry out the reactions between 50° to 60° C. As would be expected, the time required for the reaction differs according to the reaction temperature, the compounds used in the reaction and the solvents. Typically, however, both reactions require between 30 minutes and 48 hours and preferably between 1 and 24 hours to run to completion Once the reaction is complete, the desired product may be isolated from the reaction mixture by conventional techniques. For example, the product may be extracted from the final aqueous reaction mixture using an organic solvent such as cyclohexane, chloroform, or ethyl acetate and then isolated by column chromatography using media such as activated carbon, silica gel, ion exchange resins, dextran bridge polymer, styrene, or acrylate ester porous polymers

EXAMPLE 1

Synthesis of 4-chlorosulfonyl-7-fluoro-2,1,3-benzoxadiazole.

3.0 g of 7-fluoro-2,1,3-benzoxadiazole were dissolved in 10 ml of chloroform and then 11.0 ml of chlorosulfonate at 0° C. were dripped into the solution. After reacting at room temperature for one hour, the solution was stirred and reacted for an additional two hours. Next, the reaction solution was transferred to 200 g of ice water, and extracted with chloroform very quickly. The extract was then water washed and dried with magnesium sulfate before filtering. The filtrate was then reduced pressure concentrated. The remaining extract was subjected to silica gel column chromatography (chloroform as mobile phase; 2 cm×60 cm) in 5 ml fractions. The respective fractions were analyzed using thin layer chromatography (silica gel, chloroform). The fraction having an R$_f$ value of about 0.5 was then collected and reduced pressure concentrated. 4.0 g of a pale brown needle-shaped crystalline substance with a melting point of between 64° and 66° C. were obtained.

Elemental analytical values for the C$_6$H$_2$N$_2$O$_3$ClFS were:

|  | C | H | N |
|---|---|---|---|
| Theoretical Value (%) | 30.46 | 0.85 | 11.84 |
| Actual value (%) | 30.48 | 0.61 | 11.70 |

EXAMPLE 2

Synthesis of 7-fluoro-4-aminosulfonyl-2 1,3-benzoxadiazole (ABD-F).

1 g of the compound obtained in Example 1 was combined with 1 ml of 28% ammonia water which was dripped in under while being chilled. After reacting for 1 hour at 0° C., 50 ml of water were added. The impurities were then removed by filtration, and then the filter solution was condensed under reduced pressure. The remaining substance was subjected to chloroform - acetonitrile (volume to volume ratio 1:1) silica gel column chromatography (2 cm×60 cm) to make 2 ml fractions. The fractions were then subjected to thin layer chromatography (silica gel, chloroform-acetonitrile (volume to volume 1:1)). The fractions having an Rf value in the vicinity of 0.75 were collected and reduced pressure concentrated. The resulting substance was recrystallized using (a 2:1 ratio) of benzene and hexane. This resulted in 0.4 g of white colored plate-shaped crystals.

Elemental analytical values for the $C_6H_4N_3O_3FS$ were:

|  | C | H | N |
|---|---|---|---|
| Theoretical Value (%) | 33.18 | 1.86 | 19.35 |
| Actual Value (%) | 33.11 | 1.82 | 19.27 |

EXAMPLE 3

Synthesis of 7-fluoro-4-N,N-dimethylsulfonyl-2,1,3-benzoxadiazole:

1.0 mg of the substance obtained in example 1 was combined with a 40 g chilled aqueous solution of dimethylamine and allowed to react at 0° C. for 30 minutes. Next, 100 ml of 1N hydrochloric acid were added, followed by extraction with ethyl ether. After water washing, the ethyl ether layer was isolated, and dried with magnesium sulfate. After filtering, the filter solution was reduced pressure condensed. The remainder was subjected to silica gel column chromatography (2 cm×60 cm) with chloroform as the mobile phase. 2 ml fractions were prepared and subjected to thin layer chromatography (silica gel, chloroform). Fractions with Rf values in the vicinity of 0.41 were collected and reduced pressure concentrated. After washing the remainder with n-hexane, it was recrystallized from a hexane - benzene (ratio 95:5) solution. The resulting 0.3 g of yellow needle shaped crystals had a melting point of between 161° and 162° C.

Elememental analysis of the $C_8H_8N_3O_3$ was:

|  | C | H | N |
|---|---|---|---|
| Theoretical Value (%) | 39.18 | 3.29 | 17.13 |
| Actual Value (%) | 39.37 | 3.23 | 17.29 |

EXAMPLE 4

Synthesis of 7-fluoro-4-phenoxysulfonyl-2,1,3-benzoxadiazole (SBD-SO3ph).

1.0 g of the compound obtained in Example 1 and 1 g of phenol were dissolved in 5 ml of benzene. Next, after dripping in a chilled mixed solution of 5 ml of benzene and 1 ml of pyridine, the solution was allowed to react for 4 hours at room temperature. After dripping in 50 ml of chilled 10% hydrochloric acid, the solution was extracted with benzene, water washed, and then dried with magnesium sulfate and reduced pressure concentrated. The remaining solid was subjected to chloroform mobile phase; silica gel column chromatography (2 cm ×60 cm) to prepare 2 ml fractions. These were then subjected to thin layer chromatography (silica gel, chloroform) and the fractions with an Rf range in the vicinity of 0.73 were collected. After reduced pressure condensation, the substance was recrystallized using n-hexane. The resulting 0.4 g of white needle shaped crystals had a melting point of between 120° to 121° C.

Elemental analysis values of $C_{12}H_7N_2O_4FS$ were:

|  | C | N | H |
|---|---|---|---|
| Theoretical Values (%) | 48.98 | 2.40 | 9.52 |

|  | C | N | H |
|---|---|---|---|
| Actual Value (%) | 49.17 | 2.38 | 9.47 |

EXAMPLE 5

Synthesis of 4-benzyloxysulfonyl-7-fluoro-2,1,3-benzoxadiazole.

1 g of the compound obtained in Example 1 was dissolved along with 1 ml of benzyl alcohol in 5 ml of benzene. Next, a mixed solution of 1 ml of pyridine and 5 ml of benzene were dripped in and allowed to react at room temperature for 1 hour. After the reaction, 50 ml of a 10% aqueous hydrochloric acid solution were dripped in, and then, the mixture was extracted with chloroform, water washed, and dried with magnesium sulfate before being reduced pressure concentrated. The remainder was subjected to silica gel column chromatography (benzene mobile phase, column 2 cm×60 cm) to prepare 2 ml fractions. These fractions were then subjected to thin layer chromatography (silica gel, chloroform) and those having an Rf value in the vicinity of 0.71 were collected, condensed under reduced pressure, and then recrystallized using n-hexane and benzene (ratio 95:5). The resulting 0.4 g of white plate-shaped crystals had a melting point of 160° to 161° C. Elemental analysis of the $C_{13}H_9N_2O_4FS$ was:

|  | C | H | N |
|---|---|---|---|
| Theoretical Value (%) | 50.65 | 2.94 | 9.09 |
| Actual Value (%) | 50.64 | 2.93 | 9.22 |

The 4-acetyl derivative of 2,1,3-benzoxadiazole can be prepared by Friedal-Crafts acylation as follows:

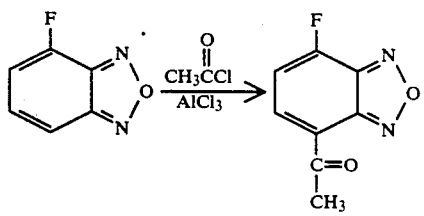

As with all Friedal-Crafts acylation reactions, an excess of $AlCl_3$ is required since the ketone product forms an acid-base complex with the catalyst.

The 4-cyano derivative of 2,1,3-benzoxadiazole can be prepared by the Sandmeyer Reaction as follows:

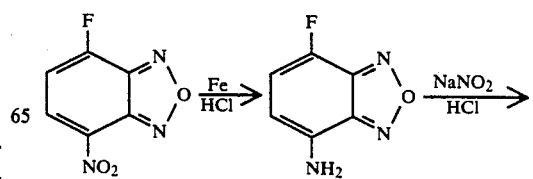

-continued

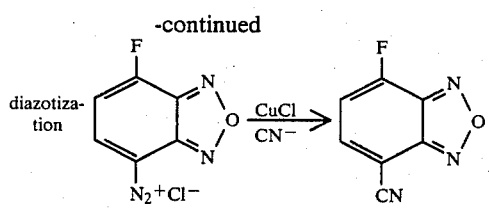

The 4-carboxymethyl derivative of 2,1,3-benzoxadiazole can be prepared by carrying out one or more hydrolysis reactions followed by esterification with methanol or reaction with diazomethane according to the following sequence:

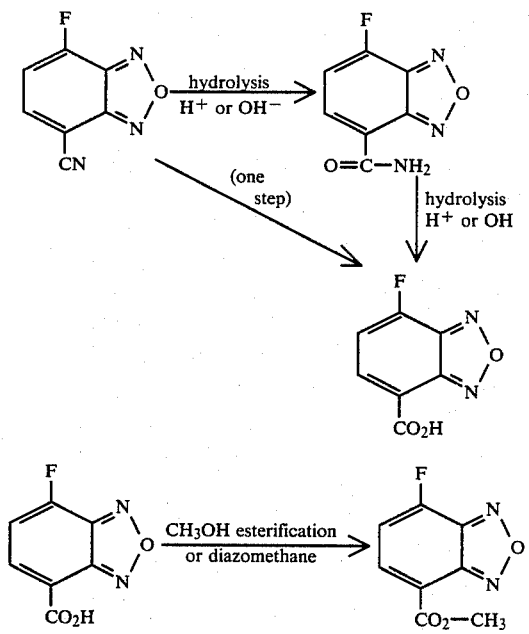

2. Formation of the fluorescent adducts

The compounds of the present invention are not, by themselves, fluorescent. Rather, fluorescence will be observed only after the fluorogenic reagents are selectively reacted with a thiol or an amine to form the fluorescent adduct (fluorophore). The reaction should be carried out under the following conditions:

(1) The reaction medium should be alkaline, preferably with a pH between 8 and 10.

(2) The reaction temperature should be at least 20° C., and preferably between 30° and 70° C., with a reaction time between 1 and 60 minutes, and preferably 5 and 15 minutes.

(3) Preferably, a buffer solution is added to the reaction system in order to maintain the pH. Such solutions include, for example, borate buffer solution, tris salt buffer solution or carbonate buffer solution.

EXAMPLE 6

Formation of the ABD-homocysteine adduct 30 ml. of a solution containing 0.14 g (1 mmol) of homocysteine in 0.1 M borate (pH 9.5, Na+) containing 1 mM ethylenediaminetetracetic acid disodium (EDTA-2Na) were combined with 0.22 g (1 mmol) of ABD-F in 30 ml of $CH_3CN$. After heating the reaction mixture for 30 min. at 60° C., the mixture was cooled on ice water and extracted with 300 ml. benzene to remove excess reagent. The residue was chromatographed in a Bio-gel P-2 column (200–400 mesh, 6×2 cm., $H_2O$ eluent). The fluorescent fractions comprising to ABD-homocysteine were collected, evaporated, and recrystallized from $H_2O$ to yield yellow needles. Relative fluorescence intensities of 2.3 M ABD-homocysteine dissolved in the buffers of various pHs were measured at 515 nm with excitation at 390 mn. As is demonstrated by FIG. 1, relatively high fluorescent intensities were observed from a pH of 2 to a pH of 7. The highest fluorescent intensities were observed at about a pH of 2.

EXAMPLE 7

Formation of ABD-F and SBD-$SO_3$ph-N-acetyl-L-cysteine adduct (1) Preparation of Fluorogenic Reagent Solutions (A) 2.9 mg of SBD-$SO_3$ph were dissolved in enough acetonitrile to make a total of 1.0 ml of solution.

(B) 2.2 mg of ABD-F were dissolved in enough acetonitrile to make a total of 1.0 ml of solution.

(2) Preparation of the Samples to be Examined

An aqueous solution containing 16.3 mg of N-acetyl-L-cysteine and 1 mM of EDTA to make a total volume of 100 ml was prepared. Next, 1 ml of this was taken and added to 1 mM EDTA in a 0.1 M borate buffer solution (pH =8.0) so that the total volume was 10 ml.

(3) The (2) solution as prepared above was divided into two 5 ml parts. They were reacted with 0.5 ml respectively of the (1)-A reagent and the (1)-B reagent at 60° C. for 30 minutes. Next, 0.1 ml of each of these reaction solutions were taken, and they were added to appropriate buffer solutions of a 0.05M concentration which had differing pH buffering ranges to make a total of 1 ml of each of the solutions. Fluorescence was then measured. In a similar manner, the fluorescence of a blank sample was measured. The results appear in Table 1.

After the completion of the reaction, the pH of the solution was decreased in order to obtain a strong fluorescence. The results, which are clear in the table, indicate that the strongest fluorescence is obtained at a pH of 2.2. Such a result is consistent with that obtained in Example 6 where homocysteine was combined with ABD-F and the highest fluorescent intensity was observed at a pH of about 2.

TABLE I

| pH at measurement time | FLUORESCENT STRENGTH | |
|---|---|---|
| | SBD-$SO_3$ph *Ex: 390 nm, Em: 500 nm | ABD-F Ex: 370 nm, Em: 490 nm |
| 2.2 | 43.5 | 39.5 |
| 3.1 | 38.0 | 23.2 |
| 5.0 | 23.4 | 12.2 |
| 7.1 | 15.5 | 9.1 |
| 8.0 | 12.2 | 8.1 |
| 8.6 | 10.9 | 5.6 |
| 9.1 | 11.0 | 3.8 |

*Ex: Excitation Wavelength
Em: Fluorescence Wavelength

EXAMPLE 8

Reactivity of ABD-F and SBD-$SO_3$ph with N-acetyl-L-cysteine (1) Preparation of the Fluorogenic Reagent (A) 2.9 mg of SBD-$SO_3$ph were dissolved in enough acetonitrile to make 10 ml of solution.

(B) 2.2 mg of ABD-F were dissolved in enough acetonitrile to make 10 ml of solution.

(2) Preparation of the Test Samples 16.3 mg of N-acetyl-L-cysteine were dissolved in enough 1 mM EDTA aqueous solution to make 100 ml. Next, 1 ml portions of this solution were taken. One was placed in a pH 8.0 borate buffered 1 mM solution of EDTA, while the other was added to a pH 9.5 buffered solution so the overall volume of the two samples was 100 ml (The former was called Sample I and the latter Sample II).

(3) 1 ml of each of Sample I and Sample II prepared as described in (2) above were added to 1 ml of the (1) fluorogenic reagent solution and incubated for various time intervals between 5 and 30 minutes at 60° C. The reaction solution was then adjusted with 0.1 N hydrochloric acid to pH 2.0, after which, fluorescence was measured. The results appear in FIG. 2.

Both ABD-F and SBD-SO$_3$ph reached the maximum fluorescent intensity at between 20 and 30 minutes at pH 8.0. Maximum was reached at between 5 and 15 minutes at pH 9.5. Also, both exhibited a nearly constant fluorescent intensity after reaching their maximum level.

EXAMPLE 9

Formation of ABD-proline and SBD-SO$_3$ph-proline adducts 11.5 mg of L-proline, which is a secondary amino acid, were dissolved in 100 ml of H$_2$O. 1 ml of that solution was then combined with enough 0.1 M borate buffer solution (pH 8.0) to make 100 ml of total solution. 1 ml of the above buffered proline solution was then combined with 10 ml of solution containing 2.9 mg of SBD-SO$_3$ph in CH$_3$CN. Likewise, 1 ml of the buffered proline solution was combined with 10 ml of a solution containing 2.2 mg of ABD-F in CH$_3$CN. Each of these solutions was then incubated at 60° C. for intervals between 5 and 60 minutes, the pH being adjusted using 0.4 ml of 0.1 N hydrochloric acid. The results appear in FIG. 3. In the Figure, net fluorescent strength is compared to each of the fluorogenic reagents reacting for 60 min. at 60° C. which was indexed at 100. The fluorescent strength is shown relative to that index.

The salient features of the present invention may be more readily appreciated by reference to the following comparative examples.

COMPARATIVE EXAMPLE 1

The reaction rates of homocysteine with ABD-F (the present invention) and SBD-F and SBD-Cl (prior art fluorogenic reagents) were compared. 1 ml of each of the above reagents in 0.1 M buffer (phosphate or borate) was combined in a 5 ml glass tube with 1.0 ml of 10μm homocysteine in a 0.1 M buffer (phosphate or borate) containing 2mM EDTA.2Na. The tube was capped and heated to a temperature between 40° and 60° C. in a water bath. At fixed reaction time intervals, the tube was taken out and cooled in ice water. The fluorescence intensities were measured at ambient temperature with emission at 515 nm (excitation at 390 nm). A reagent blank without thiol was treated in the same manner. Pseudo-first-order rate constants for each sample were calculated based on the difference in fluorescence intensities, i.e., sample fluorescence minus blank fluorescence, from that of the authentic derivatives (ABD-homocysteine or SBD-homocysteine).

As shown in Table II, the reaction rate with ABD-F was over 30 times faster than that with SBD-F, and was approximately 3 orders of magnitude faster than that with SBD-Cl. In the case of SBD-Cl at pH 7.0 or 8.0, the reaction rate was not calculated because of the low yield of fluorescence. When the organic solvent such as CH$_3$CN was added to reaction medium, the rate was not increased remarkably.

As depicted in FIG. 2, the reaction of homocysteine with ABD-F was completed quantitatively in 5 minutes at 40° to 50° C. and pH 8.0 without decrement of fluorescence intensities over the 60 min. tested. The gradual hydrolysis of ABD-F at higher pH and longer reaction time necessitates the use of as short a reaction time as possible.

TABLE II

Comparison of the Reaction Rate Constants of Homocysteine with Various Reagents (ABD-F, SBD-F or SBD-Cl)

| | k, min$^{-1}$ | | | | |
| --- | --- | --- | --- | --- | --- |
| | ABD-F | | | SBD-F | SBD-Cl |
| pH | 40° C. | 50° C. | 60° C. | 60° C. | 60° C. |
| 7.0 | 2.54 × 10$^{-2}$ | 7.40 × 10$^{-2}$ | 1.16 × 10$^{-1}$ | 3.55 × 10$^{-3}$ | ND$^b$ |
| 8.0 | ND$^b$ | ND$^b$ | ND$^b$ | 2.31 × 10$^{-2}$ | ND$^b$ |
| 9.5 | ND$^b$ | ND$^b$ | ND$^b$ | 8.01 × 10$^{-2}$ | 2.39 × 10$^{-3}$ |

$^a$Homocysteine (5 μM) and the reagent (500 M) were reacted in 0.1 M buffer (phosphate or borate) containing 1 mM EDTA · 2Na Fluorescence measurement: Ex, 390 nm; Em, 515 nm. Buffers: phosphate (sodium dihydrogen phosphate and disodium hydrogen phosphate), borate (borax and HCl or NaOH).
$^b$ND, not determined.

COMPARATIVE EXAMPLE 2

The reactivity of the SBD-SO$_3$ph and ABD-F solutions prepared in Example 9 were compared to that of a solution containing 2.0 mg NBD-Cl (a known compound) added to enough CH$_3$CN to make 10 ml of solution. The three test solutions were each combined with 1 ml of the L-proline solution previously described. After allowing to incubate at 60° C. for intervals between 5 and 60 minutes, the pH was adjusted using 0.4 ml of 0.1 N HCl. The results appear in FIG. 3 which compares the net fluorescent strength to each of the fluorogenic reagents reacting for 60 min. at 60° C., which was indexed at 100. The fluorescent strength shown is relative to that index.

The figure clearly shows that the reactivity of the compound of this invention with respect to amine is higher or at least equal to that of the NBD-Cl of the prior art.

3. Detection and Measurement of the Fluorescent Adducts

As previously indicated, the fluorogenic reagents are themselves not fluorescent. This is important to the practice of the invention since it would likely interfere with the assay.

Thus, it is the substitution of the fluoro group of the compounds of this invention with the thiol or amine which renders the benzoxadiazole moiety fluorescent. In order to measure the intensity of the fluorescence, the excitation wavelength and fluorescent light wavelength, when the compound of this invention is bonded with the thiol, should be an excitation wavelength of between 360 and 410 nm, and preferably, between 370 and 400 nm, while the fluorescent wavelength should be between 480 and 530 nm and preferably, between 490 and 520 nm. When the inventive compounds are bonded with amines, the excitation wavelength should be between 430 and 480, preferably between 440 and 470 nm, while the fluorescent wavelength should be between 530 and 580 nm, and preferably between 540 and 570 nm.

As is evident from Table III, where the fluorescent intensities of biologically important thiols are listed, the different thiols each have different excitation and emission maxima ranging from 374–389 nm and 500–519 nm respectively. As is also evident, cysteamine exhibited the highest relative fluorescent intensity whereas captopril exhibited the lowest.

TABLE III

Relative Fluorescence Intensities and Maximal Wavelengths for Various Thiols Using ABD-F[a]

| thiol | $\lambda mas^{nm}$ Ex | Em | RFI[b] |
|---|---|---|---|
| cysteamine | 377 | 504 | 127 |
| mercaptoethanol | 389 | 519 | 122 |
| α-mercaptopropionylglycine | 377 | 505 | 119 |
| coenzyme A | 389 | 513 | 118 |
| glutathione | 381 | 512 | 108 |
| homocysteine | 382 | 511 | 100 |
| N—acetylcysteine | 375 | 508 | 65 |
| cysteine | 374 | 500 | 62 |
|  |  |  | 65[c] |
| captopril | 381 | 511 | 58 |
| cystine |  |  | ND[d] |
| alanine |  |  | ND[d] |
| proline |  |  | ND[d] |

[a]Thiol (5 μM) and ABD-F (500 μM) were reacted in 0.1 M borate (pH 8.0, Na+) containing 1 mM EDTA.2Na at 50° C. for 5 min. After the reaction, 0.6 mL of 0.1 M HCl was added and measured (final pH 2).
[b]Ex, 380 nm; Em, 510 nm.
[c]Ex, 375 nm; Em, 500 nm.
[d]ND not detected. Fluorescence intensity in homocysteine was arbitrarily taken as 100.

The fluorescent thiol and/or amine adducts of the present invention may be separated from other components in an analytical sample using high performance liquid chromatography and then detected fluorometrically. Alternatively, the adducts may be formed after the HPLC separation has been completed. Such techniques are known and typically involve an initial determination of the characteristic elution time of each of the authentic analytes taken separately, which time period is then used to identify the analytes present in a mixture. Such techniques are described in detail in the "Liquid Chromatographic Determination of Amino and Imimo Acids and Thiols by Post column Derivatization with 4-Fluoro-7-nitrobenzo-2,1,3-oxadiazole" from *Analytical Chemistry*, Vol. 55, p. 1786 (1983) (Post column derivatization using NBD-F) and "High-Performance Liquid Chromatography and Fluorometric Detection of Biologically Important Thiols, Derivatized with Ammonium 7-Fluorobenzo-2-oxa-1,3-diazole-4-sulphonate (SBD-F) (Pre-column treatment)."

Of course, the inventive compounds may also, be used in conjunction with conventional column chromatography techniques. It will also be appreciated that in situations where only one or two of the analytes are present in a medium to be studied, no separation will need to be carried out whatsoever, as where it is desired to detect a single thiol in the presence of several amines.

Because of the rapid and complete reaction of the fluorogenic compounds of the present invention with amine and thiol analytes as well as the high fluorescence quantum yield of the product so formed, it is possible to detect very minute amounts of analytes, i.e. in the picomole range, using conventional analytical equipment. Such equipment includes commercially available liquid chromatography fluorescence detectors or commercially available spectrofluorometers with flow cells.

EXAMPLE 10

Preparation of ABD-Thiol complexes and separation and detection of same 1.0 ml of a solution containing 1 millimole of ABD-F in a 0.1 molar borate buffer having a pH of 8.0 was added to a 5 ml glass tube. A 1.0 ml solution containing mixed thiols in a 0.1 molar borate buffer containing 2 millimoles of EDTA.2Na having a pH of 8.0 was combined with ABD-F solution. The mixed thiol solution contained the following 5 components:

| Thiol | micromoles |
|---|---|
| cysteine | 2.16 |
| glutathione | 2.08 |
| N—acetylcysteine | 2.57 |
| homocysteine | 1.92 |
| cysteamine | 2.46 |

After all the above reagants were combined, the reaction tube was vortex mixed, capped, and heated at 50° C. for 5 minutes. After cooling the tube in ice water, 0.6 ml of 0.1M HCl was added to the solution thus lowering the pH to 2. A 10 microliter aliquot of the acidic solution was then injected into a Waters high-performance liquid chromatographic system, equipped with a U6K universal injector and a Model 600 A pump. A Bondapak $C_{18}$ (300×3.9 mm i.d.) connected to a guard column of Bondapak $C_{18}$-Corasil (20×3.9 mm. i.d.) was used at ambient temperature. The eluting solvent was acetonitrile - 0.05 M potassium biphthalate (pH 4.0) (8:92). The flow rate was 1.0 ml/min and the eluate was monitored at 510 nm with excitation at 380 nm. Separation of all the components was complete after 35 minutes.

Figure 4:
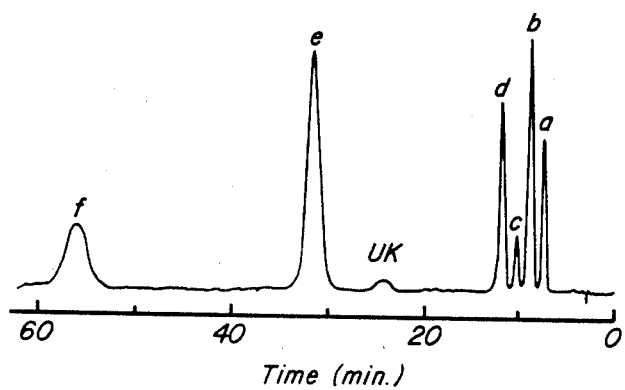
FIG. 4 is a chromatogram of biological thiols derivatized with ABD-F.

As would be expected, the retention times of ABD derivatives were decreased by increasing the acetonitrile concentration as well as the pH. FIG. 4 is a chromatogram of the completely separated thiols. Peaks a–e represent the 5 different thiols. Peak f was confirmed to be the excess ABD-F. The small unknown peak eluted at about 24 minutes is believed to be the hydrolysis product of ABD-F. Under the conditions described, the detection limits (signal to noise ratio of 3) for ABD-cysteine, ABD-glutathione, ABD-N-acetylcysteine, ABD-homocysteine, and ABD-cysteamine were 0.6, 0.4, 1.9, 0.5, and 0.5 pmol respectively.

Thus, it is possible to use the compound of this invention to detect trace quantities of thiol and/or amine. The compounds of the present invention can also be used to detect thiol and/or amine in a wide range of tissues when they are examined in a microscope, so it is a useful histological examination tool for thiol and amines contained in protein, for peptide quantification, and as an active site probe for enzymes containing -SH groups in the active site. It can also be used to evaluate membranes, cells and tissue by detecting the thiol and/or amine in the substances, and in addition, it can be used for thiol and/or amine in excretions so it is useful to study metabolism or in clinical analyses. It therefore has a broad range of application in biochemistry, physiology and in clinical medicine.

Although only preferred embodiments are specifically illustrated and described herein, it will be appreciated that many modifications and variations of the present invention are possible in light of the above teachings and within the purview of the appended claims without departing from the spirit and intended scope of the invention.

What is claimed is:

1. A compound having the general formula:

wherein X is

—CN, —CO$_2$CH$_3$, or SO$_2$R, and wherein R is

—OR$_3$ or —Cl; R$_1$ and R$_2$ are hydrogen atoms or alkyl groups having 1 to 3 carbon atoms and R$_3$ is a phenyl or benzyl group.

2. The compound as defined by claim 1, having the general formula:

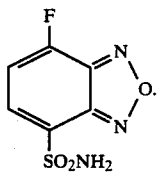

3. The compound as defined by claim 1 having the general formula:

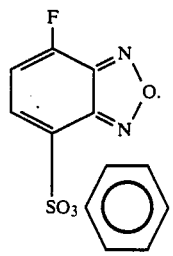

4. A method of detecting and measuring at least one of thiols, primary amines and secondary amines present in a liquid comprising the steps of:
   (i) providing a biological fluid containing analytes comprising at least one of thiols, primary amines and secondary amines;
   (ii) reacting said analytes with a fluorogenic reagent of the formula;

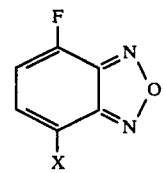

wherein X is

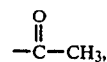

—CN, —CO$_2$CH$_3$, or SO$_2$R, and wherein R is

—OR$_3$ or —Cl; R$_1$ and R$_2$ are hydrogen atoms or alkyl groups having 1 to 3 carbon atoms and R$_3$ is a phenyl or benzyl group; whereby a fluorescent adduct is formed;
   (iii) assaying said fluorescent adducts by a fluorescent analytical method.

5. The method of claim 4 further comprising the step of isolating each of the analytes in said biological fluid prior to said reaction step.

6. The method of claim 4 wherein the step of isolating each of said analytes in said analytical fluid is carried out by high performance liquid chromatography.

7. The method of claim 6 wherein each of the analytes is isolated before forming said fluorescent adduct.

8. The method of claim 6 wherein each of the analytes is isolated after forming said fluorescent adducts.

9. The method of claim 4 wherein said fluorescent analytical method is carried out using a spectrofluorometer or a liquid chromatography fluorescence detector.

* * * * *